United States Patent
Mostaghel

(10) Patent No.: US 6,536,258 B1
(45) Date of Patent: Mar. 25, 2003

(54) BLAST LOAD SIMULATION SYSTEM

(75) Inventor: Naser Mostaghel, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 09/432,938

(22) Filed: Nov. 3, 1999

Related U.S. Application Data

(60) Provisional application No. 60/106,973, filed on Nov. 4, 1998.

(51) Int. Cl.[7] .......................... G01P 15/00; G01N 3/34; G01M 7/00
(52) U.S. Cl. .................... 73/12.01; 73/12.06; 73/12.13
(58) Field of Search .................... 73/12.01, 12.04, 73/12.05, 12.06, 12.13; 338/42; 440/111

(56) References Cited

U.S. PATENT DOCUMENTS

| | | | |
|---|---|---|---|
| 3,407,746 A | * | 10/1968 | Abildgaard ................. 417/486 |
| 3,577,763 A | * | 5/1971 | Beal ............................... 73/12 |
| 3,601,935 A | * | 8/1971 | Cadwell ........................... 52/2 |
| 3,871,208 A | * | 3/1975 | Berg .......................... 73/12.13 |
| 3,974,313 A | | 8/1976 | James |
| 3,998,016 A | | 12/1976 | Ting |
| 4,027,436 A | | 6/1977 | Daly |
| 4,308,695 A | | 1/1982 | Ehrsam |
| 4,382,247 A | * | 5/1983 | Stecher et al. ................. 338/42 |
| 4,405,020 A | * | 9/1983 | Rassieur ....................... 173/89 |
| 4,414,777 A | | 11/1983 | Masacchia |
| 4,432,285 A | | 2/1984 | Boyars et al. |
| 4,433,522 A | | 2/1984 | Yerushalmi |
| 4,451,321 A | * | 5/1984 | McKelvey .................. 156/382 |
| 4,565,089 A | * | 1/1986 | Arciszewski et al. ....... 73/12.13 |
| 4,579,004 A | * | 4/1986 | Kalthoff et al. ............... 73/799 |
| 4,662,289 A | | 5/1987 | Harder |
| 4,718,356 A | | 1/1988 | Caspe |
| 4,860,572 A | * | 8/1989 | Brar et al. ...................... 73/12 |
| 4,928,468 A | | 5/1990 | Phillips |
| 5,019,443 A | * | 5/1991 | Hall ............................ 156/106 |
| 5,173,374 A | | 12/1992 | Tiedemann et al. |
| 5,206,451 A | | 4/1993 | Bocker |
| 5,450,742 A | * | 9/1995 | Baltz et al. ................. 73/12.06 |
| 5,567,867 A | * | 10/1996 | Nazar ........................... 173/90 |
| 5,741,970 A | * | 4/1998 | Rubin ...................... 73/379.05 |
| 5,833,782 A | * | 11/1998 | Crane et al. .................. 156/60 |
| 5,975,972 A | * | 11/1999 | Wilsem ....................... 440/111 |

* cited by examiner

Primary Examiner—Hezron Williams
Assistant Examiner—Lilybett Martir
(74) Attorney, Agent, or Firm—MacMillan, Sobanski & Todd, LLC

(57) ABSTRACT

A blast load simulation system includes a glass panel having two surfaces. The system also includes a membrane for covering at least one of the two surfaces of the glass panel. The system also includes means for delivering an impulse with a given characteristic to the glass panel through the membrane.

25 Claims, 3 Drawing Sheets

BLAST LOAD SIMULATION SYSTEM

This application claims the benefit of Provisional application No. 60/106,973, filed Nov. 4, 1998.

FIELD OF THE INVENTION

This invention relates in general to the testing of glazing, and more particularly, a blast load simulation system for testing of glazing, such as glass windows, under various conditions.

BACKGROUND OF THE INVENTION

One of the major causes of injury and loss of life in structures subjected to blast loading is the glass windows. Common window glass is annealed glass. When annealed glass is subjected to impact loads such as the one generated by a blast, it breaks into relatively large shards with sharp cutting edges. This is responsible for most of the injuries incurred in explosions. In the tragic bombing of the Alfred P. Murrah Federal Building in Oklahoma City in April 1995, more than 75% of the injuries sustained by those who survived in the area surrounding the building were due to flying shards of glass.

Recent research has been exploring the use of high-strength glazing materials such as polycarbonates, laminated glass and tempered glass. Tempered glass fractures at higher pressure levels than annealed glass, and it breaks into small cubed-shaped fragments. The small fragments are presumed to be less lethal. However, the capacity of tempered glass to resist higher pressure levels means that, when the glass fails, the broken pieces have far more energy, and thus become far more lethal. Also, due to their capacity to resist higher blast pressure, tempered glass windows can transfer far greater loads to the structure's frame, thereby increasing the possibility of the structure's collapse. To preserve the advantage of a tempered glass window fracturing in small cube-shaped pieces and to reduce its capacity to withstand high blast pressures, researchers at Sandia National Laboratories have proposed various ways of inducing early onset of fracture in tempered glass at lower pressure levels. They have carried out a limited number of tests (using explosives of different sizes) to verily their concept.

Currently, the test facility to carry out these tests is either a shock tube or an open-air arena. The ASTM Standard F1642-96, Standard Test Method for Glazing and Glazing Systems Subject to Airblast Loadings states, "Open air arenas should be sited on clear and level terrain. The Test facility shall be situated, and be of sufficient size, to accommodate the detonation of the required amount of explosives to provide the desired peak positive pressure and positive phase impulse. The test director shall ensure that potential environmental impact issues are determined and resolved prior to testing. The test director shall ensure that testing is conducted at ambient temperature in accordance with section I.1".

Section I.1 specifies the ambient temperature as 75±20° F. Clearly, qualification with the above testing facility is very expensive. The main obstacle hampering the development of standardized tests for various conditions for glazings, such as glass windows, for blast loading continues to be the limitations imposed by the need to test for explosions of different characteristics.

It is an object of the invention to provide a realistic, simple, safe, and economical physical simulation technique for testing glass panels under various conditions.

It is another object of the invention to provide a technique that can generate pressure shocks simulating blasts of different magnitudes and durations.

It is yet another object of the invention to provide a simulation system that can be used to research the capacity of various glazing as well as other panels to resist blast loading.

It is still another object of the invention to provide a simulation system that can also be used to develop standardized tests for structural elements such as walls, panels, glazing and glass windows subjected to blast loads.

It is still yet another object of the invention to provide a simulation system that can be used to verify computer models.

It is another object of the invention to provide a simulation system that can be used to locally test and quality the sensitivity of glass windows for various environmental conditions, such as temperature.

SUMMARY OF THE INVENTION

This invention relates to a blast load simulation system for testing of glazing, such as glass windows, under various conditions. The system comprises a glazing having two surfaces, a membrane for covering one of the two surfaces of the glazing, and means for delivering an impulse with a given characteristic to the glazing through the membrane.

A method of testing glazing against blast loads comprises the steps of:

a) providing a membrane and a glazing with an airtight chamber formed therebetween;

b) filling the airtight chamber with a fluid medium; and c) delivering an impulse with a given characteristic to the glazing through the membrane.

Various objects and advantages of this invention will become apparent to those skilled in the art from the following detailed description of the preferred embodiment, when read in light of the accompanying drawings.

DETAILED DESCRIPTION OF THE PREFERRED EMBODIMENT

In general, the forces imparted to an above ground structure by any given set of free-field incident and dynamic pressure pulses can be classified into four general components: (a) the force resulting from the incident pressure, (b) the force associated with the dynamic pressures, (c) the force resulting from the reflection of the incident pressure impinging upon an interfering surface, and (d) the pressures associated with the negative phase of the shock wave. In the invention, only the reflected pressure is considered because it is the largest pressure generated by a blast. In general, air blast imparts horizontal, vertical, and overturning motions to structures in its path. Both vertical and overturning motions are assumed to be small and are not considered in this simulation.

Figure 1:
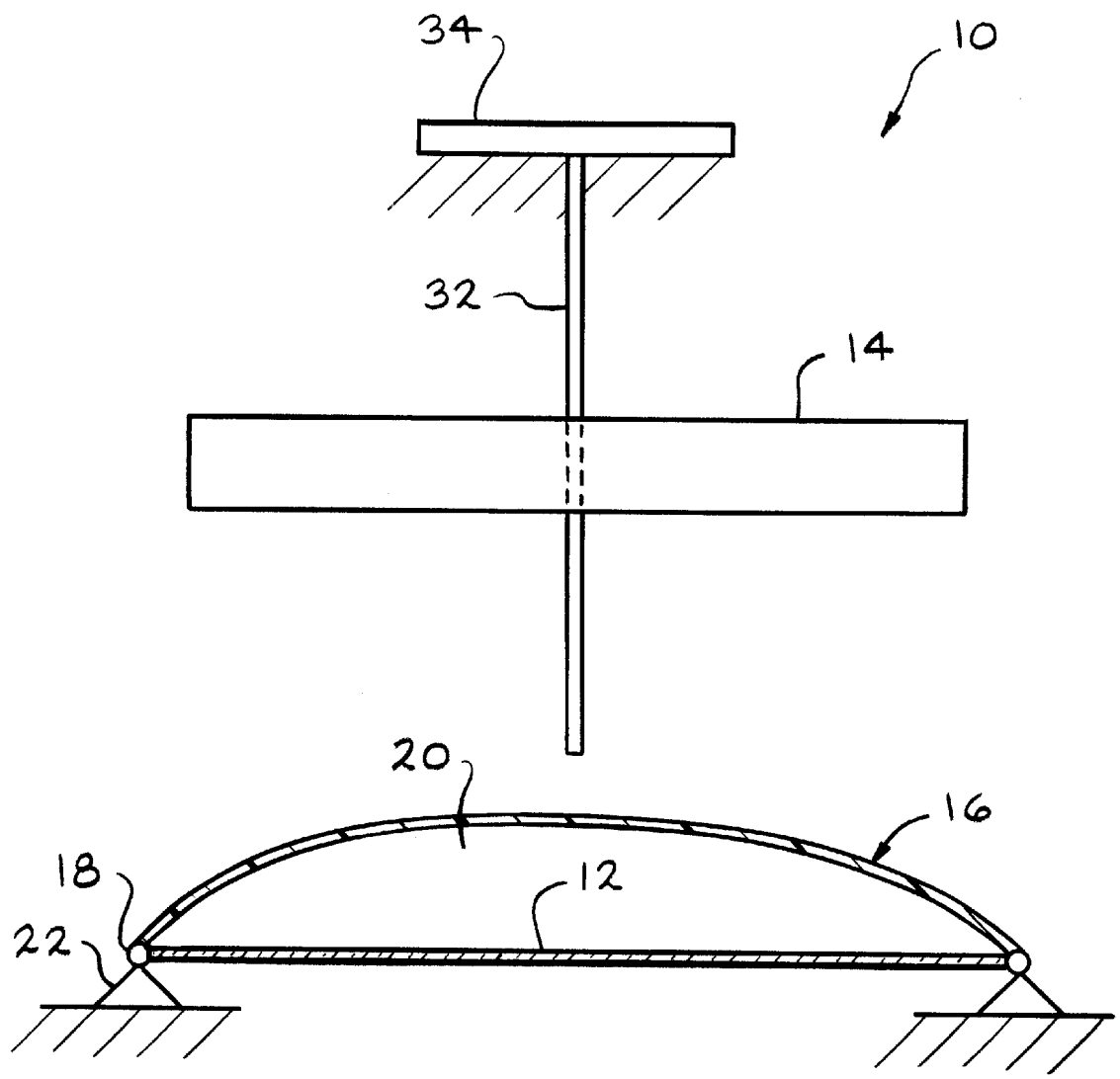
FIG. 1 is schematic view of the blast simulation system according to a preferred embodiment of the invention.

Referring now to the drawings, there is illustrated in FIG. 1 a blast simulator system, shown generally at 10, for testing glazing and glazing systems, such as a glass panel 12, under various blast load conditions. To simulate blast loads on the glass panel 12, the blast simulator system 10 includes a weight 14, such as a plate, which can be dropped from different heights on top of a membrane 16 as a means for delivering an impulse with a given characteristic, such as magnitude and duration, to the glass panel 12 through the membrane 16.

In a first preferred embodiment of the invention, the membrane 16 is made of a single piece of elastomeric material, such as neoprene rubber. The membrane 16 and the glass panel 12 are mounted within a frame system 18 such that the membrane 16, in conjunction with the frame system 18, covers one or more of the surfaces of the glass panel 12 to form an airtight chamber 20 therebetween. Preferably, the airtight chamber is inflated by filling the membrane 16 with a fluid medium, such as a gas or liquid, and more preferably the airtight chamber 20 is filled with air. In this manner, the membrane 16 can be inflated to different initial pressures to select the impulse duration. The frame system 18 can, in turn, be supported by a support system 22 of a type well-known in the art.

Figure 2:
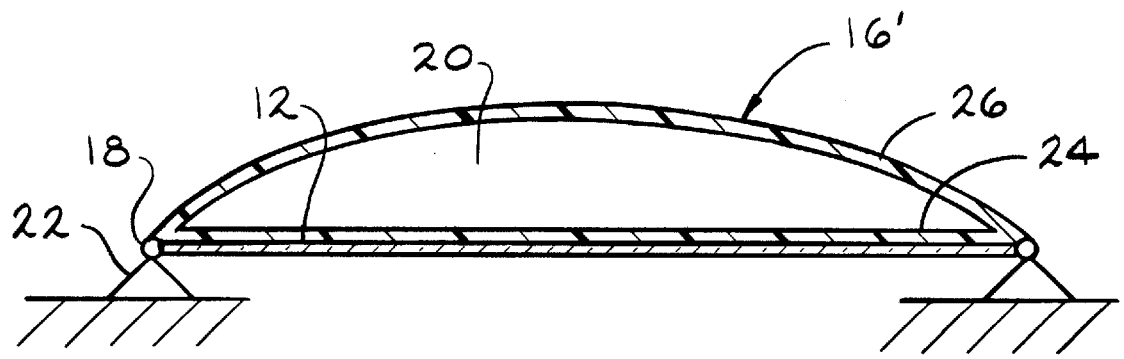
FIG. 2 shows an alternate embodiment of the membrane of FIG. 1.

It should be realized that the membrane 16 can be arranged in several different configurations. For example, a membrane 16' can consist of a lower membrane member 24 adjacent the glass panel 12 and an upper membrane member 26 positioned above the lower membrane member 24 so as to form the airtight chamber 20 therebetween, as shown in FIG. 2. The upper membrane member 26 can have the same thickness as the lower membrane member 24 or the lower membrane member 24 may have a thickness smaller than the upper membrane member 26 to provide a more efficient transfer of the impulse from the weight 14 to the glass panel 12. Because the upper and lower membranes 24, 26 form an airtight chamber 20 therebetween, this alternative embodiment alleviates the problem that may occur of forming the airtight chamber 20 by using the single membrane 16 in conjunction with the frame system 18.

Figure 3:
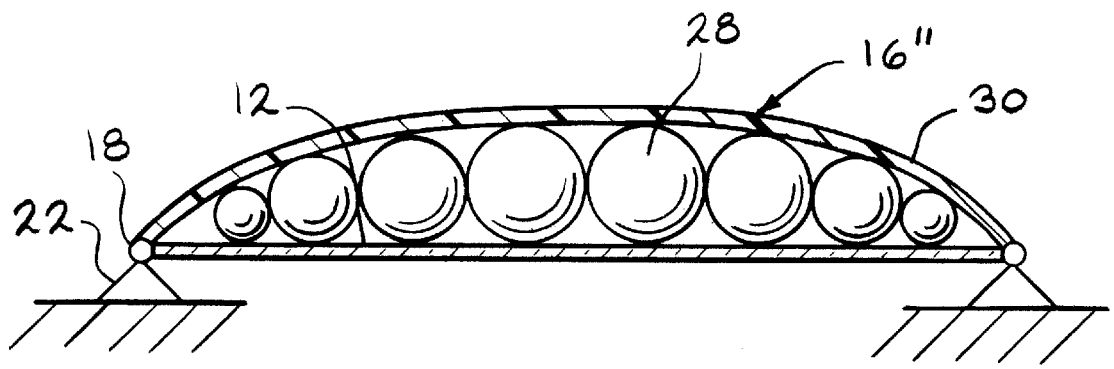
FIG. 3 shows another alternate embodiment of the membrane of FIG. 1.

In another alternative embodiment, a membrane 16" may consist of one or more cells 28 that are encapsulated with an outer membrane 30, such as an elastomeric material, as shown in FIG. 3. The elastomeric material may be made of neoprene, as in the membranes 16, 16'. Preferably, the cells are spherical in shape. However, the cells may be formed in any desired shape. Each cell 28 comprises a separate airtight chamber 20 that can be inflated with the liquid or gas fluid, preferably air. Alternatively, one or more of the cells 28 can be fluidly connected to each other to provide a controlled deflation of the ruptured membrane 16". The advantage of using the membrane 16" having one or more cells 28, rather than the membranes 16, 16', is that the integrity of the simulation system 10 to transfer the impulse from the weight 14 to the glass panel 12 is maintained even if one or more of the cells 28 is ruptured by a projectile. Thus, the membrane 16" is especially useful in certain blast conditions, such as a tornado or a hurricane, where flying debris forming projectiles travelling at high velocities may impinge the membrane 16".

Referring now to FIG. 1, the weight 14 is slidably mounted to a linear guide member 32. The guide member 32 preferably has one end secured to a frame structure 34 to ensure that the weight 14 strikes the membrane 16 at the proper location when the weight 14 is released. By changing the mass and the drop height of the weight 14, impulses of desired magnitudes can be generated. Also, the impulse duration can be selected by changing the drop height and the initial pressure under the membrane 16.

As illustrated in FIG. 1, the glass panel 12 is tested in a horizontal position. Alternatively, the glass panel 12 can be tested in a vertical position by using a pendulum or any other similar device to deliver the impulse to the glass panel 12. In either case, the simulator system 10 is capable of delivering impulses of different magnitude and duration in the form of plane pressure shocks. The magnitude of the impulse can be enhanced by augmenting the weight or the pendulum with stored energy devices, such as springs (not shown).

Neglecting the friction between the guide member 32 and the weight 14, consideration of the balance of energy yields $$I_i = mv = m\sqrt{2gh} \tag{1}$$

where, $I_i$ is the incident impulse, m is the mass of the failing weight, g is the acceleration of gravity, and h is the drop height.

$$i_i = \frac{I}{A} = \frac{m}{A}\sqrt{2gh} = \overline{m}\sqrt{2gh} \tag{2}$$

where,

A is the area of the panel, and $\overline{m}$ is the mass per unit area of the panel.

Pressure transducers (not shown) and strain gauges (not shown) can be mounted on the glass panel 12. The time history of the pressure can be used to calculate the specific reflected impulse. The magnitude of this impulse is the area under the pressure time-history, which is given by $$i_r = \int_0^{\tau_d} P(t)\,dt \tag{3}$$

where, $i_r$ is the reflected impulse,

P(t) is the pressure between the membrane and the glass panel, and $z\tau_d$ is the positive phase duration.

The specific incident and reflected impulses as well as the pressure generated by various weights of explosive (TNT equivalent) at different distances from a target have been measured and are well-known in the art. This data can be used to define and interpret the input incident impulse in light of the measured data.

A series of static tests was conducted to verify the mathematical model described above. The static test was performed on a square aluminum plate (23¾×23¾ inches and ¼ inches thick). The aluminum used had similar mechanical properties to those of the glass panel 12, but it could be statically loaded to a much higher load.

Figure 4:
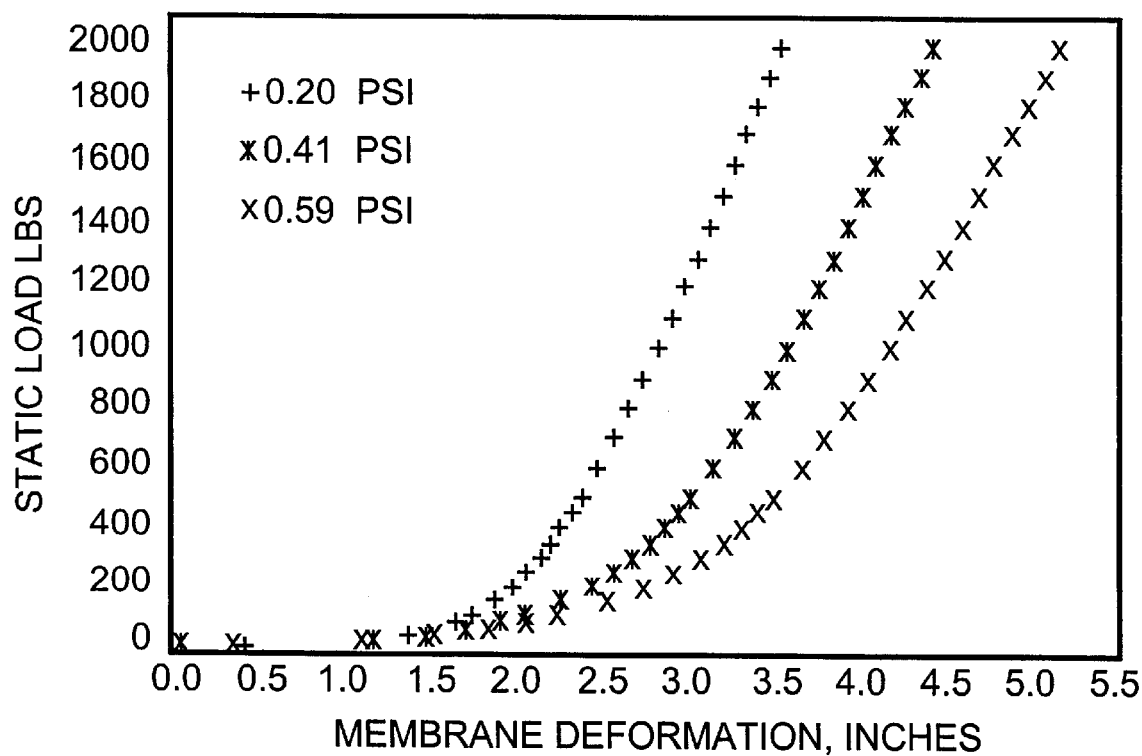
FIG. 4 is a diagram of the relationship between static load and membrane deformation for a series of static tests conducted using the preferred embodiment of the invention.

The membrane 16 was inflated with an initial pressure and the initial membrane deformation was measured. The plate 14 was then placed on the top of the inflated membrane 16. The plate 14 was then leveled and the deformation due to weight of the plate 14 was measured. For three different initial pressures under the membrane 16, increments of static load was applied on the top of the plate 14 and the corresponding deformation of the membrane 16 was recorded. The static load versus membrane deformation for all three different initial pressures is shown in FIG. 4. The three initial pressures are given in pounds per square inch (psi). This relationship describes the stiffness of the simulation system 10, which is then used in the mathematical model.

The following references are hereby incorporated by reference in their entirety:

Physical Injuries and Fatalities Resulting from the Oklahoma City Bombing, JAMA, Vol. 276, p.382, Aug. 7, 1996.

Handbook of Glass in Construction, Joseph S. Amstock, McGraw-Hill, 1997.

Lessons From the Oklahoma City Bombing, Defensive Design Techniques, Eve E. Hinman, David J. Hammond, American Society of Civil Engineers, 1997.

Protecting Buildings From Bomb Damage, Committee on Feasibility of Applying Blast-Effects Mitigation Technologies and Design Methodologies from Military Facilities to Civilian Building, National Academy Press, Washington D.C., 1995.

Dynamics of Window Glass Fracture in Explosions, Edwin K. Beauchamp, Rudolph V. Matalucci, Sandia National Laboratories, Sandia Report, SAND98-0598, UC-700, May 1998.

Device for Base Isolating Structures from Lateral and Rotational Support Motion, N. Mostaghel, U.S. Pat. No. 4,633,628 (Jan. 6, 1984).

Standard Test Method for Glazing and Glazing Systems Subject to Airblast Loadings, American Society for Testing and Materials (ASTM), ASTM F1642-96 (under jurisdiction of ASTM Committee F-12 on Security Systems and Equipment).

Structures to Resist the Effects of Accidental Explosions, Army TM 5-1300, Navy NAVFAC P-397, AFR 88-22, Department of the Army, the Navy, and the Air Force, November 1990.

The patents and documents referenced herein are hereby incorporated by reference in their entirety.

In accordance with the provisions of the patent statutes, the principle and mode of operation of this invention have been explained and illustrated in its preferred embodiment. However, it must be understood that this invention may be practiced otherwise than as specifically explained and illustrated without departing from its spit or scope.

What is claimed is:

1. A blast load simulation system comprising:
   a glass panel having two surfaces;
   a membrane for covering at least one of the two surfaces of the glass panel, the membrane defining a chamber for containing a fluid medium; and
   a means for striking the membrane, wherein the membrane is adapted to deliver an impulse with a known characteristic to the glass panel through the fluid medium in response to being struck by the means for striking, thereby simulating a blast load to the glass panel.

2. The system of claim 1 wherein said delivery means comprises a guide member and a weight slideably mounted to the guide member.

3. The system of claim 1 further comprising a frame system, wherein said membrane comprises a single piece of elastomeric material mounted to the frame system to form an airtight chamber therebetween.

4. The system according to claim 3, wherein the airtight chamber is filled with a fluid medium.

5. The system according to claim 1, wherein said membrane comprises an upper membrane member and a lower membrane member adjacent said glass panel to form an airtight chamber therebetween.

6. The system according to claim 5, wherein the airtight chamber is filled with a fluid medium.

7. The system according to claim 1, wherein said membrane comprises one or more cells encapsulated by an outer membrane, each cell forming an airtight chamber therein.

8. The system according to claim 7, wherein each airtight chamber is filled with a fluid medium.

9. A method of testing a structural element selected from the group of walls, panels, polycarbonate panels, glass panels, laminated glass panels, and tempered glass panels against blast loads, the method comprising the steps of:
   connecting a membrane to the structural element in a manner that defines an airtight chamber formed therebetween;
   introducing a fluid medium into the airtight chamber; and
   delivering an impulse with a known characteristic to the membrane, wherein the impulse is transmitted through the fluid medium to the structural element.

10. The method according to claim 9, wherein the membrane comprises a single piece of elastomeric material.

11. The method according to claim 9, wherein the membrane comprises an upper membrane member and a lower membrane member adjacent said structural element to form the airtight chamber therebetween.

12. The method according to claim 9, wherein the membrane comprises one or more cells encapsulated by an outer membrane, each cell forming the airtight chamber therein.

13. The method according to claim 9, wherein the fluid medium is air.

14. The method according to claim 9, wherein the impulse is delivered by a weight slidably mounted on a guide member.

15. A method of testing a structural element selected from the group of walls, panels, polycarbonate panels, glass panels, laminated glass panels, and tempered glass panels against a blast load, the method comprising the steps of:
   connecting a membrane to the structural element in a manner that defines an airtight chamber formed therebetween;
   introducing a fluid medium into the airtight chamber; and
   delivering a blast load force with a known characteristic to the structural element.

16. A method of testing a glass panel against a blast load, the method comprising the steps of:
   providing a membrane and a glass panel with an airtight chamber formed therebetween;
   introducing a fluid medium into the airtight chamber; and
   delivering blast load force with a known characteristic to the glass panel,
   wherein the blast load force is delivered by a guide member and a weight slideably mounted to the guide member.

17. A blast load simulation system comprising:
   a structural element selected from the group of walls, panels, polycarbonate panels, glass panels, laminated glass panels, and tempered glass panels;
   a membrane for covering a surface of the structural element, the membrane defining a chamber for containing a fluid medium; and
   a means for striking the membrane, wherein the membrane is adapted to deliver an impulse with a known characteristic to the structural element through the fluid medium in response to being struck by the means for striking, thereby simulating a blast load to the structural element.

18. The system according to claim 17 wherein said delivery means comprises a guide member and a weight slideably mounted to the guide member.

19. The system according to claim 17 further comprising a frame system, wherein said membrane comprises a single piece of elastomeric material mounted to the frame system to form an airtight chamber therebetween.

20. The system according to claim 19 wherein the airtight chamber is filled with a fluid medium.

21. The system according to claim 17 wherein the membrane comprises an upper membrane member and a lower membrane member adjacent said structural element to form an airtight chamber therebetween.

22. The system according to claim 21 wherein the airtight chamber is filled with a fluid medium.

23. The system according to claim 17 wherein the membrane comprises one or more cells encapsulated by an outer membrane, each cell forming an airtight chamber therein.

24. The system according to claim 23 wherein each airtight chamber is filled with a fluid medium.

25. A blast load simulation system comprising:

a structural element selected from the group of walls, panels, polycarbonate panels, glass panels, laminated glass panels, and tempered glass panels;

a membrane connected to the structural element in a manner that defines an airtight chamber formed therebetween; and a means for striking the membrane, wherein the membrane is adapted to deliver an impulse with a known characteristic through the airtight chamber to the structural element in response to being struck by the means for striking, thereby simulating a blast load to the structural element.

* * * * *